(12) United States Patent
Tayot

(10) Patent No.: US 7,709,017 B2
(45) Date of Patent: May 4, 2010

(54) IMPLANTABLE PREPARATIONS

(75) Inventor: Jean Louis Tayot, La Tour de Salvagny (FR)

(73) Assignee: Khorionyx, La Tour de Salvagny (FR)

( * ) Notice: Subject to any disclaimer, the term of this patent is extended or adjusted under 35 U.S.C. 154(b) by 47 days.

(21) Appl. No.: 11/499,723

(22) Filed: Aug. 7, 2006

(65) Prior Publication Data

US 2007/0031474 A1    Feb. 8, 2007

Related U.S. Application Data

(60) Provisional application No. 60/774,607, filed on Feb. 21, 2006.

(30) Foreign Application Priority Data

Aug. 5, 2005    (FR)   ................................... 05 08392

(51) Int. Cl.
     *A61K 9/00*          (2006.01)
     *A61K 38/17*        (2006.01)

(52) U.S. Cl. .................... 424/422; 424/426; 424/444; 424/486; 424/499; 514/21; 530/385

(58) Field of Classification Search .................. None
See application file for complete search history.

(56) References Cited

U.S. PATENT DOCUMENTS

| | | | |
|---|---|---|---|
| 2,460,550 A | 2/1949 | Strumia et al. | |
| 2,597,432 A | 5/1952 | Beniams et al. | |
| 2,912,359 A * | 11/1959 | Anigstein et. al. | .......... 424/529 |
| 4,746,730 A * | 5/1988 | De Ambrosi et al. | ........ 530/385 |
| 5,108,908 A * | 4/1992 | Coves et al. | ............... 435/68.1 |
| 5,665,383 A * | 9/1997 | Grinstaff et al. | ............ 424/450 |
| 6,977,231 B1 * | 12/2005 | Matsuda | ..................... 442/370 |
| 2002/0122816 A1 * | 9/2002 | Sung et al. | .................. 424/445 |
| 2003/0125532 A1 * | 7/2003 | Yoshii et al. | .................. 536/20 |
| 2004/0248774 A1 * | 12/2004 | Tayot | ............................ 514/2 |
| 2004/0265371 A1 * | 12/2004 | Looney et al. | .............. 424/464 |

FOREIGN PATENT DOCUMENTS

| | | |
|---|---|---|
| FR | 2 854 801 | 11/2004 |
| JP | 62 195400 | 8/1987 |

\* cited by examiner

*Primary Examiner*—Jeffrey E Russel
(74) *Attorney, Agent, or Firm*—Stites & Harbison PLLC; Stephen J. Weyer

(57) ABSTRACT

An implantable preparation comprises a material which can be obtained from globin that has been modified, especially chemically, to be, at least partially, soluble at physiological pH. The material is biocompatible, and biodegradable in the organism. The material may be soluble at physiological pH, or insoluble at that pH. The preparation may be in the form of a solution, suspension, paste, gel, film, sponge, powder or granules, or a solid implant. The preparation can be used for the healing, protection or filling of external skin wounds, the filling of wrinkles and skin flaws, the filling of tissue, as a device for fixing prostheses or biomaterials, or as a device for preventing adhesion.

38 Claims, No Drawings

IMPLANTABLE PREPARATIONS

The present application claims the benefit of U.S. Provisional Application No. 60/774,607 filed on Feb. 21, 2006 and French Application No 05 08392 filed on Aug. 5, 2005, both of which are hereby incorporated by reference herein.

TECHNICAL FIELD

The object of the present invention is to provide new globin preparations that can be used for administration to humans in the form of implants. These preparations may, in particular, be in the form of injectable powders, pastes, gels, suspensions and solutions or implantable solid materials, which are intended especially to correct wrinkles or to protect or fill wounds and help them to heal. Various biopolymers or biomaterials are currently available for such applications.

BACKGROUND OF THE INVENTION

Numerous medical applications of collagen have already been described, whether in the form of pastes, for example for filling purposes, fluid or solid formulations, such as films or compresses, or in the form of various implants. In fact, only animal collagen is generally used.

The preparation of human collagen, which would be preferable to animal collagen for the avoidance of immunological and inflammatory reactions, is possible from human skin tissue. However, it is made very difficult because the removal of human tissue from corpses poses considerable ethical problems and requires expensive tests in order to eliminate the risk of the transmission of infectious, viral or other diseases. The preparation of human collagen from placentas is expensive, complex and difficult to organize. The preparation of human collagen by modern methods of genetic recombination or of cell culture is also very expensive, which will certainly hamper the commercial development of this product.

Globin that is insoluble at physiological pH and not chemically modified has recently been described as an alternative to collagen in some medical applications: (patent FR 2854801). Globin is the protein which constitutes haemoglobin, which itself contains 4 peptide chains ($2\alpha$ chains and $2\beta$ chains) each associated with a haem. Haem is formed by a tetrapyrrole structure containing 1 positively charged iron atom. There are 4 haems per molecule and they are responsible for the red colour of haemoglobin.

Processes for the preparation of globin have been known for a very long time and were developed for the purpose of application in foodstuffs or for the preparation of injectable pharmaceutical solutions.

Unlike haemoglobin, which is completely soluble at physiological pH, globin is remarkably insoluble under the same conditions. The insoluble, or poorly soluble, character of globin under physiological conditions has hitherto hampered the development of its medical applications as plasma substitutes. This is why the majority of published tests have sought to prepare soluble derivatives of globin at physiological pH, especially by succinylation using succinic anhydride or by acetylation using acetic anhydride, or by hydrolysis of the amide groups at alkaline pH. All of those processes increase the negative charge of globin and reduce its isoelectric pH, rendering the globin soluble at neutral pH.

An injectable product combining a soluble preparation of acidic globin with insulin has been developed, patented and marketed: REINER (1939); REINER et al. (1939). After injection, the product permits gradual release of insulin from this complex: RABINOWITCH et al. (1947); BERG et al. (1953). The globin of which this preparation is composed is not chemically modified; it is insoluble at physiological pH, present at a low concentration, and it is neither the active element nor the main element of this product.

Recently, new materials and new medical applications based on globin that is insoluble at neutral pH under physiological conditions have been described and have been the subject of a family of patents arising from patent FR 2854801.

However, it seemed to us that it would be of value to be able to manufacture biomaterials that are soluble or insoluble as desired, at physiological pH, using one and the same starting material derived from globin.

The present invention proposes to provide new materials and preparations implantable in the organism which are prepared from globin that is chemically modified to be soluble at physiological pH. These implants do not have the disadvantages or limitations of the known materials and formulations, for example of collagen, sodium hyaluronate, or the like, in particular owing to the ability to prepare them from the blood of the patient to be treated or from one of his matches and owing to their natural and completely tolerated character.

SUMMARY OF THE INVENTION

The invention relates to an implantable preparation which is completely or partially soluble or insoluble and which can be formulated in various forms, comprising a material which can be obtained from globin that is modified, especially chemically, to be at least partially, and preferably completely, soluble at physiological pH, the material being biocompatible, preferably sterile, and biodegradable. Physiological pH is understood to mean, in particular, a pH of from 6 to 8, preferably from 6.5 to 7.5 and preferentially the range of the physiological pHs. Implantable is understood to mean the ability to be implanted in the organism, in tissue or in contact therewith, including on the skin or on external wounds, intravascular administration being excluded.

DESCRIPTION OF PREFERRED EMBODIMENTS

The modified globin is preferably modified to be completely soluble at physiological pH but it may also be modified, for example starting from insoluble globin originating from haemoglobin, only in a more limited manner but one which makes it distinctly hydrophilic and partially soluble.

The implantable preparations according to the invention are preferably completely sterile but they may also not be sterile, especially when they originate from autologous biological samples taken from the patient himself. These matters of sterility form part of the ordinary knowledge of the specialized implant expert, especially where the care of a chronic skin wound is concerned.

The sterilization can be achieved in particular by beta or gamma irradiation, for example in a form frozen in the presence of dry ice, or by autoclaving, especially at 120° C.

In one embodiment, the material that can be obtained from globin modified to be soluble at physiological pH is this modified globin itself.

In another embodiment, this material may be obtained by rendering insoluble the modified globin that is soluble at physiological pH.

These soluble or insoluble preparations are especially in the form of an injectable paste or gel for implantation, implantable solid materials, for example powder, granules, or films. They may be soluble in a physiological liquid or rendered insoluble after chemical crosslinking of the soluble globin. Injectable is understood to mean the property of being able to be injected in order to effect local implantation, with the exception of any intravenous or intra-arterial injection, which are strictly contra-indicated.

Preferably, in order to be rendered soluble at physiological pH, the globin is modified chemically by alkaline treatment, especially using sodium hydroxide, and/or by esterification of the carboxylic groups, and/or acetylation or succinylation, to which processes its amine groups are sensitive. In addition, the globin may be rendered partially soluble by a partial chemical reaction or an alkaline incubation which is briefer, or at a concentration lower than 1N. By way of example, treatments in sodium hydroxide NaOH having a concentration of from 0.1 to 1N for from 4 to 24 hours at ambient temperature are possible. When the concentration of sodium hydroxide, or of another alkaline base, is increased, the incubation time and/or the temperature may be reduced.

In one embodiment, the material is substantially soluble at physiological pH and in that case the material preferably is or comprises the globin modified to be soluble at physiological pH.

In another embodiment, on the other hand, the material is substantially insoluble at physiological pH, preferably by being obtained by crosslinking the globin soluble at physiological pH.

In another embodiment, the preparation comprises both one of the materials soluble at physiological pH and one of the materials insoluble at physiological pH.

In other embodiments, the preparation may comprise another material, especially a filling material, which is biocompatible, sterile and insoluble at physiological pH, especially globin that is biodegradable, for example sterile, and insoluble at physiological pH, as defined in FR-A-2 854 801.

The said other material may also be selected from the group constituted by collagens, chitosan and oxidized celluloses, or generally filling or tissue-augmentation materials.

The preparation may be in the form of a suspension, paste or gel, which is preferably sufficiently fluid to be injectable.

However, in other embodiments it may be in a solid form, for example in the following forms:

powder or granules,
film, membrane or mesh,
sponge,
preformed solid implant.

It may also be in the form of an injectable solution and in that case, if the globin modified to be soluble at physiological pH is present and forms the main active constituent, it is preferable for the concentration of the globin to be at least 10%, preferably greater than or equal to 12 or 15%.

The preparation may comprise a globin powder modified to be soluble at physiological pH. It may then also comprise a crosslinking agent, it being possible for the mixture to form a glue which adheres to organic tissue. The crosslinking agent may itself be in the form of a powder, it being possible for the whole to form a glue in the presence of a liquid medium, especially a physiological liquid.

A preparation comprising the globin modified to be soluble at physiological pH may also comprise a solid material which is insoluble at physiological pH and which is obtained from the said globin and/or another solid material, namely biodegradable sterile globin insoluble at physiological pH.

This other material may be in the form of a powder.

These preparations comprising the globin powder modified to be soluble at physiological pH may be formulated as a dry aerosol or spray, or the modified globin may be associated with a solid dressing.

Preferably, an injectable preparation comprises globin modified to be soluble at physiological pH.

However, a preparation comprising globin modified to be soluble at physiological pH may also be produced in the form of a woven fabric, a knitted fabric, a mesh, a sponge or a film which are implantable and optionally reinforced by a suturable implantable material.

It may comprise another biocompatible solid material, especially collagen, chitosan or oxidized cellulose, or else a solid material insoluble at physiological pH which is obtained from the said globin or from the globin which is biodegradable, preferably sterile, and insoluble at physiological pH according to FR-A-2 854 801.

If the material is insoluble at physiological pH, the preparation may also be formulated as a powder, for example as a dry aerosol or spray.

A preparation comprising a material which is insoluble at physiological pH and obtained from globin modified to be soluble at physiological pH can be produced in the form of a film which is optionally reinforced by a suturable material, or in the form of a solid implant which is obtained, for example, by crosslinking a gel or a foam of globin modified to be soluble at physiological pH.

In another embodiment, a preparation comprising a material which is insoluble at physiological pH and obtained from globin modified to be soluble at physiological pH may comprise a fluidizing or lubricating agent and may be in the form of a suspension, paste or gel. The fluidizing agent may be hyaluronic acid (which also implies its equivalents, hyaluronates), carboxymethylcellulose or gelatin.

Advantageously, the fluidizing agent may be globin modified to be soluble at physiological pH.

A liquid preparation comprising a solution of globin modified to be soluble at physiological pH may be produced in the form of a liquid aerosol or spray, or in solution associated with a dressing.

Such preparations in which the globin modified to be soluble at physiological pH is in solution may comprise a crosslinking agent in order to form a glue which adheres to organic tissue.

They may also be in the form of a foam and comprise a crosslinking agent in order to form a glue which adheres to organic tissue.

In general, the biological glues according to the invention may also contain an adhesive agent, especially hyaluronic acid or carboxymethylcellulose.

The preparations comprising globin modified to be soluble at physiological pH may also comprise a solid material and may be in the form of a sponge, mesh, woven fabric, knitted fabric, or film, which are optionally reinforced by a suturable material, this other material preferably being selected from the group of textiles formed by threads manufactured from resorbable or non-resorbable polymers, such as polyesters, polyalkenes, the families of the polyhydroxy acids, collagens, chitosan and oxidized celluloses. The said other material may also be obtained from globin modified to be soluble at physiological pH and may be rendered insoluble at physiological pH, or also it may comprise biodegradable globin insoluble at physiological pH.

Advantageously, the adhesive preparations forming a biological glue may be in the form of a kit comprising, in separate containers, the material soluble at physiological pH and the crosslinking agent.

The preparations according to the invention may be in a one-piece form, preferably ready for use. However, they may also be in the form of two or more components which are to be combined or mixed, for example, in the form of a kit, preferably in sterile form. For example, separate containers or syringes may contain the material obtained from modified globin and another component, for example a fluidizing agent or a viscosity agent, a crosslinking agent or an adhesive agent.

The value of this new family of products resides in particular in the fact that they are protein biomaterials which may be soluble or insoluble, as desired, and which are prepared from a defined, pure and homologous protein which is completely biocompatible with the surrounding tissue into which they are injected. This protein, when it is of natural origin, must undergo chemical modification before being used in order to render it soluble at physiological pH.

The medical applications permitted by these biomaterials prepared from chemically modified globin are numerous. Furthermore, these applications are unexpected because no product derived from globin has hitherto been marketed in the form of an implantable biomaterial for medical or surgical applications. This unexpected character is all the more surprising since globin represents approximately 75% of all of the proteins of the blood (corpuscles+plasma) and since only the plasma proteins, representing the remaining 25%, are used today in medicine. Among these, albumin, or fibrinogen, are used for various medical and surgical applications such as: coatings, adhesives, injectable colloidal solutions, etc. . . .

Thus it is possible, e.g. to combine in a new manner the plasmatic fibrinogen based glues, said "fibrin glues", such as Tisseel®, Tissucol®, Quixil®, Hemaseal®, Beriplast® and others, with adhesive or non adhesive globin material. This opportunity allows a rational use of the blood proteins which may help to avoid wasting, decrease the required dosages, improve their results and increase their applications. These surgical glues according to the invention thus comprise a content of fibrinogen based material, which is preferably lower than the usual content, and a soluble or insoluble material obtainable from modified globin, according to the invention, or even non modified insoluble globin.

In numerous applications of the invention, the material obtained from the above-mentioned modified globin acts as an active constituent, or even a main or exclusive active constituent, owing to its physiological interaction, especially at the cellular level, with the tissue in or on which it is implanted.

Homologous human globin may be preferable to heterologous animal globin and therefore allows optimum avoidance of any immunological reaction of the patient to be treated, during or after implantation. This product therefore represents an important advantage over collagen which has hitherto been prepared from animal skins (calf, pig, etc . . . ) and which requires a certain number of precautions and conditions to prevent immunological reactions in the patients: the necessity to test each patient for a possible allergy to animal collagen and the impossibility of treating persons who are allergic.

Chemically modified globin soluble at physiological pH may be filtered under sterile conditions through porous membranes. For appropriate concentrations of from 1 to 50% (10 to 500 mg/ml) such solutions may be treated as solutions of proteins and they permit the manufacture of products such as: sponges, films, granules, powders, various solids, using or combining the techniques of drying, lyophilization, crosslinking, precipitation. Some examples are set forth below.

Globin is easy to purify from red corpuscles originating from animal or human blood. Human red corpuscles are available in large quantities from out-of-date donations remaining in stock in blood transfusion centres and for which all the preliminary health tests have been carried out at the time the blood was taken. The preparation of globin that is soluble at physiological pH and implantable, or of other insoluble biomaterials based on the same chemically modified and then crosslinked globin therefore represents a new route for satisfying biomedical applications which are developing to an increasing extent, while at the same time making good use of unused blood or out-of-date blood donations and avoiding or reducing their destruction. In contrast to other proteins, including collagens, globin that is chemically modified and soluble at physiological pH has the novel feature of preserving its soluble character despite prolonged alkaline treatment and/or despite sterilization by irradiation. This enables it to be used entirely safely, thanks to the guarantee of a powerful deactivation of the infectious or transmittable agents potentially present in any product of biological origin. This enables the biological properties of globin to be exploited in human medicine when it is necessary to use a preparation soluble at physiological pH.

The implementation of the invention is also possible starting from the taking of a blood sample from a patient to be treated of approximately from 20 to 200 ml, and its conversion into chemically modified autologous globin using the same methods as for large volumes, then its conversion into implantable biomaterial intended for applications such as the protection, filling or healing of chronic wounds, or the correction or filling of wrinkles. The number of units prepared from a sample taken from the patient may be large and may permit repeated and prolonged treatment of the patient.

For the hemolysis step of the red cells, the latter can be first purified, in order to start from a purified haemoglobin solution being already free from the plasma proteins. But this step can be avoided, specially because of the specific property of globin to remain insoluble in an aqueous solution at neutral pH, which distinguishes it from the other plasma proteins and allows it to be separated therefrom.

Likewise, the human placenta which is expelled after childbirth contains blood which is generally destroyed by incineration but which may also be used for the invention.

Pouches of donor blood are checked officially by blood transfusion authorities owing to the numerous biochemical, bacteriological, and serological examinations and screening tests for various viruses and other infectious agents. In the case of placental blood, it would clearly be necessary to carry out the same examinations on samples of blood from the umbilical cord or from the mother before being able to collect, preserve and extract the blood from this starting material. For autologous blood, the tests to be carried out can be simplified.

The implementation of the invention may first of all require the collection and purification of the red corpuscles from these blood samples, or blood liquids, by simple operations which are already known, for example in accordance with the following process.

The red corpuscles are recovered by low-speed centrifugation. The plasma supernatant is separated and replaced by a physiological saline liquid of the PBS type, containing 9 g/l of NaCl and buffered to a neutral pH. After several washes (3 to 5), the suspension of red corpuscles is thus freed from the plasma proteins. 1 or 2 volumes of distilled water are added to the residue of purified red corpuscles in order to effect an osmotic shock which brings about the lysis of the membranes of the red corpuscles and frees the haemoglobin in a concentrated and purified solution. A step of high-speed centrifugation (10 to 20,000 rpm) enables the membrane debris and cell debris in the residue to be eliminated. A final step of filtering the supernatant through a membrane having a porosity of 0.2 micron permits the preparation of a purified and sterile haemoglobin solution free from particles and derivatives of tissue, cellular or membrane origin. Other methods permit the purification of haemoglobin from frozen and haemolysed blood and the avoidance of the prior purification of the red corpuscles. Those methods have been described in the patent U.S. Pat. No. 4,764,279 and combine precipitations by ethanol and chromatography on anion exchange supports of the type DEAE Cellulose, DEAE Spherodex or other supports.

The haem-globin cleavage at acidic pH was described in the presence of alcohol by SCHULZ as early as 1898. ANSON and MIRSKY in 1930, then ROSSI-FANELLI et al. in 1958 use acetone in the presence of acid at 0° C. TEALE (1959) prefers the use of methyl ethyl ketone instead of acetone. AUTIO et al. (1984) separate the globin at acidic pH owing to the absorption and precipitation of the haem with soluble carboxymethylcellulose. The globin thus prepared is soluble at acidic or alkaline pH but becomes insoluble as soon as the pH of the aqueous solution is neutralized to pH 6 to 8.

Owing to this specific property, it becomes possible to obtain a selective precipitation of the globin in aqueous solution at neutral pH, at a low salt concentration close to 5 g/l ClNa, where at these conditions the other plasmatic proteins remain soluble, do not co-precipitate with globin and keep separated in the supernatant. This method is useful where one wishes to avoid to first separate the red cells from the plasma, which allows to freeze the blood as soon as the sample is taken.

Solubilization tests of globin at physiological pH are already known. Some were carried out by STRUMIA et al. in 1951 and 1952 by prolonged alkaline treatment which brings about partial deamidation of globin at the asparagine and glutamine residues converted into aspartic acid and glutamic acid, respectively (VARS 1952). Other solubilization tests were carried out in particular by VOLCKMANN in 1988 by succinylation. These preparations of chemically modified globin soluble at physiological pH were proposed as substitutes for plasma or albumin, by intravenous injection, in patients requiring an increase in the circulating blood volume after cirrhosis of the liver, accidental blood loss or major burns. These medical applications did not see the light of day despite satisfactory clinical development (Strumia et al., 1952) or were swiftly abandoned, in particular because they were toxic at a high dose or they were eliminated too rapidly via the renal tract. Hitherto, no-one had thought that this chemically modified globin soluble at physiological pH could be used for the manufacture of autologous or homologous implants intended especially for filling, protecting or healing internal or cutaneous wounds.

The ability to crosslink chemically modified globin that is soluble and usable at a high concentration by conferring on it an insoluble character in physiological medium explains the persistence of this form of globin after tissue implantation, which also makes it relatively resistant to enzyme degradation, especially if the amount injected is large, which is the case in filling or tissue-augmentation applications.

The value of the invention can be readily proved starting from a preparation of pig globin which has been chemically modified by prolonged alkaline treatment or by esterification of the carboxylic groups, or by acetylation or succinylation of the amine groups, then purified and dehydrated to obtain a powder which is completely soluble in physiological aqueous medium. The globin powder thus prepared may be placed in a syringe, sterilized by ethylene oxide or irradiation at a dose of from 5 to 25 or 30 kGray and redissolved at high concentration in a physiological solution of PBS. After mixing at ambient temperature with a crosslinking agent suitable for the chemical modification carried out, such as diepoxides, or aldehydes, or polyaldehydes, or oxidized polysaccharides, or other reactive groups, a viscous and adhesive gel is obtained which is completely biocompatible and biodegradable. Other known adhesive adjuvants, such as hyaluronic acid, carboxymethylcellulose, which can take an active or passive part in the constitution of the crosslinked globin lattice and are trapped therein may be added to the initial powder or the globin solution. This biological glue can advantageously replace comparable products prepared from synthetic polymers which are less well tolerated, or from collagen materials which generally require the use of heating means in order to be fluidized before use.

For ethyl-globin or other globin esters preparations, which are soluble at neutral pH, it is possible to use the preparation under the form of a concentrated solution at neutral pH, which can be prepared just before use from distinct powder and PBS syringes which are then mixed. After injection into the tissues to be filled or protected, the ester functions on the globin are rapidly hydrolyzed and the globin will recover its insoluble behaviour. This underlines the interest of esterifying the globin to submit it to a chemical modification which can be reversed by hydrolysis in an aqueous medium.

The absence of antigenicity of rabbit globin, chemically modified by succinylation, was demonstrated by immunizing rabbits with or without Freund's adjuvant subcutaneously and intramuscularly. The blood samples taken after immunization enable the absence of anti-globin or anti-haemoglobin antibodies to be verified by the usual monitoring tests: Volckmann (1988). The chemical modification of globin solubilized by prolonged alkaline treatment was documented by Vars et al. (1952) and its biocompatibility was demonstrated by Strumia et al. (1952).

EMBODIMENTS OF PRODUCTS ACCORDING TO THE INVENTION

Example 1

Preparation of Chemically Modified Rabbit Globin Soluble at Physiological pH

Five anaesthetized rabbits are bled by cardiac puncture. The blood is recovered in the presence of heparin or in the presence of sodium citrate in order to prevent its coagulation. 210 ml of blood are thus obtained and are centrifuged for 30 minutes at 2500 rpm. The supernatant containing the plasma is removed with a pipette and the residue is washed 5 times with 3 volumes of PBS buffer containing 9 g/l of NaCl and buffered to pH 7.2. An equal volume of distilled water is added, with agitation, to the final, washed, residue in order to lyse the red blood corpuscles. The final suspension is centrifuged at 12,000 rpm in order to eliminate cell and membrane debris. The supernatant is filtered through a cellulose acetate membrane having a porosity of 0.22 micron. 82 ml containing 97 g/l of haemoglobin are obtained.

The haemoglobin is converted into globin in accordance with the technique described by TAYOT and VERON (1983). This haemoglobin solution is poured with agitation into 275 ml of 96% ethanol containing 1 ml of concentrated HCl. The pH is adjusted to 3. The final concentration is 74% of ethanol and 22 g/l of haemoglobin at acidic pH. 3 g of activated charcoal L4S of the CECA brand are added with vigorous agitation over a period of 15 hours at 4° C. The suspension is centrifuged at 15,000 rpm for 30 minutes in order to eliminate the charcoal in the form of a residue. The supernatant containing the decolorized acidic globin is filtered through a series of porous membranes up to the lowest porosity (0.2 micron) in order to eliminate the fine particles of charcoal. The filtrate is then precipitated in 10 volumes of acetone. The acidic globin precipitate is washed with acetone to prepare an acidic anhydrous powder freed from the salts. 4.5 g of this powder are diluted in 100 ml of 0.25M NaOH in accordance with the publication of Strumia et al. (1951). The alkaline solution obtained after 30 minutes' agitation is clear. It is then incubated at 37° C. for 27 hours, then neutralized to a pH of approximately 7.2 by adding a hydrochloric acid solution. The neutralized solution remains clear. The globin in solution is then precipitated by adding 10 volumes of acetone. The precipitate is harvested by filtration through a porous cloth, then washed with acetone to obtain a neutral anhydrous powder spontaneously soluble in water or a physiological solution at a neutral pH.

Example 2

Preparation of Chemically Modified Human Globin Soluble at Physiological pH 200 ml of out-of-date human blood, taken on sodium citrate, are centrifuged for 30 minutes at 2500 rpm. The supernatant containing the plasma is removed with a pipette while also aspirating the whitish surface layer of cells corresponding to the leucocytes. The pellet of red corpuscles is washed 5 times with 3 volumes of physiological PBS solution, containing 9 g/l of NaCl and buffered to pH 7.2, by successive centrifugations. Two volumes of distilled water are added to the final residue to lyse the red blood corpuscles. The haemolysed suspension is clarified by centrifuging for 30 minutes at 12,000 rpm and filtered through a membrane having a porosity of 0.2 micron to give 210 ml containing 52 g/l of haemoglobin which are preserved at 4° C. This solution is slowly poured, with agitation, into 4 l of acetone containing 40 ml of 10N HCl. The suspension is agitated vigorously and left to stand for 1 hour at ambient temperature under a chemical hood. The haem dissolved in the acetone is removed by filtration through a porous cloth and the precipitate of decolorized globin is recovered, washed in acetone and dried under a stream of air.

By way of variation, various mineral acids (sulphuric, hydrochloric, phosphoric . . . ) or carboxylic acids, such as acetic acid, oxalic acid or citric acid, for example, may be used to acidify the acetone solution or the haemoglobin solution before the decolorization thereof.

Another variant of this process consists in precipitating the acidic haemoglobin solution before its decolorization. The precipitation can be effected by adding NaCl at a concentration of from 40 to 60 g/l. The acidic haemoglobin precipitate is then decolorized by suspension in a sufficient volume of ethanol and/or acetone. The pigment passes into solution in the ethanol and/or the acetone; the globin remains in a precipitated form and can be harvested by filtration through a porous cloth. Owing to the elimination of any aqueous phase, this variant enables the necessary volume of ethanol and/or acetone to be reduced by a factor of at least 5.

The acidic precipitate of decolorized globin, containing salts, is then washed with an aqueous acetone solution containing at least 90% of acetone and then washed with anhydrous acetone and dried to prepare an acidic powder freed from the salts. 4.5 g of this powder are diluted in 100 ml of 0.25M NaOH and incubated at +20° C. for 24 hours and then treated as in Example 1. The solution is neutralized to a pH of approximately 7.2 by adding a hydrochloric acid solution. The globin is then precipitated by adding at least 10 volumes of acetone. The precipitate is harvested by filtration through a porous cloth and then washed with acetone and dried in order finally to obtain a neutral powder soluble in water or a physiological solution.

Several variants permit the preparation of partially or completely soluble globin by shorter alkaline incubation or at a concentration lower than 1N. By way of example, treatments in sodium hydroxide NaOH having a concentration of from 0.1 to 1N for from 4 to 24 hours at ambient temperature are possible. When the concentration of sodium hydroxide, or of another alkaline base, is increased, the incubation time and/or the temperature must be reduced.

Example 3

Another Preparation of Human Globin, which is Modified Chemically and Soluble at Physiological pH The process of Example 1 is carried out starting from inspected and out-of-date cell pellet obtained from a blood transfusion centre. A neutral powder of human globin which is chemically modified, soluble in water or a physiological liquid, and which is biocompatible and implantable by injection or surgically is obtained.

Example 4

Another Preparation of Human Globin which is Modified by Succinylation and which is Soluble at Physiological pH This preparation is effected in accordance with the works of Volckmann (1988). The acidic precipitate of decolorized globin, containing salts, is washed with an acetone solution containing enough water to dissolve the salts without dissolving the globin and then washed with anhydrous acetone and dried in order to prepare an acidic powder freed from the salts. This powder is taken up at a concentration of 30 mg/ml in a solution of 1 g/l of NaOH containing 9 g/l of NaCl, and then 80 mg of succinic anhydride are added per gram of globin, at a temperature of 20° C. The pH decreases spontaneously to 9 where it is maintained by the gradual addition of NaOH with continuous monitoring using a pH meter. The reaction is terminated when the pH is stable. After waiting for 1 hour, the solution is adjusted to a neutral pH and precipitated by a 90% aqueous acetone solution. The precipitate is washed with anhydrous acetone and then dried. A neutral powder of globin soluble in physiological solution at a neutral pH is obtained.

Example 5

Another Preparation of Human Globin which is Modified by Esterification and which is Soluble at Physiological pH A precipitate of human globin is prepared in accordance with Example 2. The acidic precipitate of decolorized globin, containing salts, is then washed with an aqueous acetone solution containing at least 90% of acetone and then washed with anhydrous acetone and dried to prepare an acidic powder freed from the salts.

800 mg of finely divided human globin powder are weighed into a 25-ml flask to which 20 ml of anhydrous methanol containing 0.2 ml of 12N HCl are added, i.e. a final acid concentration of 0.12N. The powder remains completely insoluble under these conditions, swells a little and is well dispersed. After the flask has been hermetically plugged, it is incubated for one week at ambient temperature with moderate agitation several times a day. The globin precipitate is separated from the acidic methanol using a nylon filter having a porosity of 1 μm. The precipitate is washed twice with 20 ml of pure acetone each time and then dried in the air to obtain 740 mg of a well-divided fine powder. This powder, which is poorly spontaneously wettable, can be rapidly dissolved in 20 ml of distilled water in a small beaker. A straw-coloured clear solution having a pH of 2.8 is obtained. The neutralization of the pH of this solution by the dropwise addition of 0.5N sodium hydroxide with manual agitation and with continuous pH monitoring permits verification of the soluble character of the globin at a neutral pH of from 6 to 8, and then its massive precipitation at an alkaline pH of approximately from 9.5 to 10.

The commencement of precipitation may be observed towards pH5 when the starting powder is not finely divided. This corresponds to the partial presence of unmodified globin protected from the esterification reaction inside a large powder aggregate. The methyl globin so prepared could exhibit some toxicity at a high dose. For, in vivo, in the presence of physiological aqueous liquids, a spontaneous hydrolysis of the methyl ester groups occurs, with the release of methanol which is toxic at high doses and the gradual regeneration of the initial globin. In order to avoid this theoretical risk, the esterification reaction may be carried out by replacing the methanol with ethanol in preference to other, less reactive, alcohols. In that case, an ethyl ester of ethyl globin is obtained which is not toxic to the organism, even at a high dose. It should be noted that the globin esters so prepared are gradually hydrolysed in vivo and spontaneously regenerate the initial insoluble globin which itself will be degraded. This is therefore a completely reversible modification. It is therefore preferable to prepare such finished products in dry or non-aqueous form in order to avoid degradation prior to their use. It should also be noted that the globin esters so prepared have a very marked positive electrical charge. Their basic isoelectric point, which is close to 10, results from the more or less complete disappearance of the carboxylic groups. This property confers on them an adhesive character with respect to negatively charged tissue. These globin esters have a large amount of amine groups which can be readily crosslinked by reagents having aldehyde groups, such as glutaraldehyde, or oxidized polysaccharides. Furthermore, they can readily form stable lattices owing to strong electrostatic bonds, in the presence of any negatively charged polymer or biopolymer, such as fibrinogen, fibrin, albumin, hyaluronates, heparin or any other polysaccharide which is sulphated or rich in carboxylic groups.

Example 6

Preparation of a Sterile Powder of Chemically Modified Globin Soluble at pH 7.2

Use as a dry or liquid spray for promoting the healing of wounds.

By following one of Examples 2 to 5, a powder of chemically modified human globin soluble at neutral pH in physiological solution is prepared. This powder is packaged in stoppered sealed flasks which are sterilized, in the presence of dry ice at −80° C., by beta or gamma irradiation at a dose of from 5 to 25 or 30 kGray.

After carrying out checks, the powder remains soluble in a pH-neutral physiological solution of the PBS type up to a concentration of approximately 50%.

By way of variation, the powder may also be sterilized by ethylene oxide which permits supplementary chemical modification by grafting hydroxyethyl groups onto the globin. This powder may be applied to a skin wound by atomization in order to make good the loss of tissue substance. The soluble globin powder has adhesive properties in contact with a wound. This facilitates its use. It permits absorption of the exudates of the wound which gradually dissolve the globin powder to form a viscous solution which gradually becomes diluted. This provides nutrients which can be assimilated directly by the damaged tissue and promotes the formation of granulation tissue, which is the first step necessary in the healing process. In a variant, the powder is first of all dissolved in PBS at a high concentration, greater than 30%, and is then applied by liquid atomization. Such a solution, from 10 to 30%, can be prepared by mixing the powder and PBS in a sterile syringe before use, and then intradermically injected for filling wrinkles or for other known uses in tissue augmentation. It is of interest to use ethyl-globin for this indication because it will recover its initial insolubility after hydrolysis, thus stopping its spreading, which extends and improves its activity.

Finally, the powder or liquid of soluble globin can be used in association with a dressing suitable for the wound to be treated.

Example 7

Preparation of a Mixture of Soluble Globin Powder Such as Prepared in Example 5, and an Insoluble Globin Powder Use as an agent for filling wounds and healing.

The Example describes the preparation of this product from pig globin and its use in the healing of deep skin wounds in pigs.

Example 2 is reproduced starting from pig's blood, the red corpuscles of which are purified and then lysed in order to extract the haemoglobin. The pig globin is prepared in accordance with the procedure described in Example 2, 3, 4 or 5 and enables a globin powder, which has been modified chemically and has become soluble at physiological pH, to be obtained.

A second preparation of globin powder insoluble at physiological pH is obtained by following Example 2, with a variant which consists in omitting the alkaline treatment for chemical modification. This powder is obtained in the following manner, in accordance with the teaching of patent FR 2854801.

After the pig haemoglobin has been decolorized by an acidic acetone solution, the acidic globin precipitate is separated and then redissolved in an aqueous solution at pH 3. The solution is filtered through a sterilizing membrane having a porosity of 0.22 micron. The globin is precipitated by neutralization to pH 7.2. This neutral precipitate is dissolved, once again, in 3 volumes of 0.1M to 1M sodium hydroxide NaOH and incubated at 20° C. for 1 hour with agitation. This alkaline treatment is not sufficient to bring about a significant modification of the globin, which remains insoluble at neutral pH. The alkaline solution is then acidified to pH 3 by adding a 3N hydrochloric acid solution. The acidic globin precipitate which forms contains salts. It is washed with an aqueous acetone solution containing approximately 90% of acetone and containing enough water to dissolve the salts without dissolving the acidic globin. This washing eliminates the salts from the precipitate. The water of the precipitate is then eliminated by washing in pure acetone and the dry powder of acidic globin is obtained by evaporating the acetone under vacuum. By way of variation, a globin powder of neutralized pH, insoluble at physiological pH, prepared by aceton precipitation or by lyophilization, could be used.

2 grams of acidic globin powder (insoluble at neutral pH) are mixed with 8 grams of globin powder soluble at neutral pH, in a closed flask. The homogeneous mixture of the two powders is then sterilized by gamma irradiation at a dose of from 5 to 25 or 30 kGray and can be used directly as an agent for filling and healing external skin wounds or internal surgical wounds. Other proportions varying from 1 to 99% of soluble powder in the mixture may be used. The weight of powder applied per wound may itself vary as a function of this proportion and of the desired osmotic pumping effect on the wound.

An experiment on deep rectangular skin wounds measuring 2×3 cm and created in pigs confirms the value of this globin powder in the healing process. At least half of the volume of the wound is filled and the wounds are then covered with a non-adhesive occlusive dressing of the OPSITE® type. The body of the pig is then covered with a tight dressing which protects the wounds from any external contamination. The wounds are cleaned with physiological water every 3 to 4 days but the filling product remains completely integrated in the wound and is neither removed nor replaced.

The presence of a soluble portion in the powder permits the aspiration and draining of the physiological "exudate" fluids of the wound, which dissolve the soluble globin, hydrate and neutralize the insoluble globin powder and release nutrients important for the cells and the development of granulation tissue. The interstitial space so freed permits optimum migration and optimum cell colonization of the implant. These fluids and the cells migrate and are adsorbed on the granules of insoluble globin and promote rapid filling by the granulation tissue. This completely tolerated filling agent, which is degraded in less than two weeks, significantly reduces contraction by the lips of the wound and promotes harmonious healing in less than four weeks, characterized by complete epithelialization of good quality.

In the same manner, it is possible to prepare the same product from human globin, for use in healing the wounds of burns victims or the chronic wounds of elderly patients, ulcers of diabetic origin, or of venous or arterial insufficiency, or bedsores. The homologous character of the globin reduces to its minimum the inflammatory reaction generally observed in contact with biomaterials that are less well tolerated.

Example 8

Preparation of a Soluble Globin Powder Such as Prepared in Example 5, and Combination with a Sponge, a Woven Fabric or an Oxidized Cellulose Powder Use as a wound-filling and healing agent.

Two grams of human globin powder soluble at physiological pH are prepared in accordance with Example 5.

Mixed sponges of soluble globin and oxidized cellulose are obtained by lyophilizing a 1% aqueous suspension of oxidized cellulose at pH 7.2 containing from 0.2 to 2% of globin soluble at the same pH. The oxidized cellulose may also be in the form of a two-dimensional or three-dimensional knitted or woven fabric. The lyophilized sponges having a rectangular dimension of 5×7 cm and a thickness of 3 mm contain 105 mg of oxidized cellulose and from 20 to 210 mg of soluble globin. This product may be sterilized, for example, by ethylene oxide and used as a filling and healing agent for burns and chronic external skin or internal surgical wounds, as in the previous Example. Other biomaterials, in particular collagens, chitosan and other polymers known for the treatment of wounds may be used instead of oxidized cellulose, in combination with the soluble globin powder.

Example 9

Preparation of a Globin Solution from Chemically Modified Globin Soluble at pH 7.2

Use for filling cutaneous tissues or protecting wounds and ensuring that they are sealed 1 gram of globin powder soluble at neutral pH and prepared in accordance with Example 5 is distributed in the dry state in a 5-ml syringe. The filled and stoppered syringe is sterilized by beta irradiation (electron beam) at a dose of from 5 to 25 or 30 kGray. This syringe is connected to a second sterile syringe containing 2 ml of physiological solution, by means of a double-ended luer connector having an inside diameter of 2 mm. The solution is injected into the syringe containing the powder. Successive reciprocating movements permit the preparation of a homogeneous viscous solution of neutral globin concentrated to approximately 10 to 50%. Such a preparation at a concentration of 10 to 30% can be injected via intradermal route for filling wrinkles, or via any other route for volume augmentation of a cellular structure, the intravascular route being excluded.

A third sterile syringe containing 0.5 ml of glutaraldehyde at 0.2% or 0.5 ml of oxidized starch at 3% may be associated in parallel with the syringe containing the globin solution at a concentration from 30 to 50%, in a kit for mixing the two, components. By pushing on the two syringes at the same time, an adhesive gel or mixture is obtained which crosslinks in a few seconds or minutes and hardens. The setting time can be adjusted by the respective concentrations of globin and crosslinking agent. This adhesive may be used for the various surgical applications which require this type of product, or for covering or protecting surgical or skin wounds.

In a first variant, an adhesive adjuvant, such as hyaluronic acid or other negatively charged polymers, such as carboxymethylcellulose, may be added to the globin syringe or the syringe containing the crosslinking agent. This polymer becomes incorporated in the lattice of the globin gel at the time of the crosslinking thereof, increases the adhesive power and the viscosity thereof and promotes its adhesion to the wound to be treated.

In a second variant, the syringe containing the concentrated liquid globin may contain air or any other gas and may be mixed with the syringe containing the crosslinking agent by successive reciprocating movements from syringe to syringe immediately before being applied to the tissue to be protected, in the form of adhesive fluid foam. After a few seconds or minutes, depending on the amount of crosslinking agent and the concentration of the globin solution, the foam hardens and remains fixed to the tissue to which it has been applied. This adhesive solution or foam can be mixed together with a fibrin glue, at the time it is prepared.

This dilution of the fibrin glue allows to increase its volume without decreasing its adhesive power; the complex which is thus created owns cicatrizing and filling properties.

Example 10

Preparation of a Paste or a Crosslinked Insoluble Suspension. Application as an Agent for Filling Wounds or as an Injectable Material for Tissue Augmentation The adhesive product described in the previous Example may be applied to an external or internal wound in order to protect it or promote the healing thereof. It may also be injected by means of fine needles, before it sets, into intradermal or subcutaneous sites in order to create or restore a volume or to correct a wrinkle.

A variant for the preparation of a non-soluble injectable product consists in subjecting a suspension of soluble globin granules, which are prepared in accordance with Example 2, 3, 4 or 5, to secondary crosslinking by a crosslinking agent appropriate to the type of chemical modification of the globin, such as, for example: a diepoxide, in particular 1,4-butanediol diglycidyl ether, especially for acetyl or succinyl globin, glutaraldehyde, or a polysaccharide oxidized in the form of macromolecular polyaldehyde, in particular for the globin esters or the derivatives obtained by alkaline treatment. After crosslinking and washing at a neutral pH, the suspension having a concentration of approximately 15% may be distributed in syringes and sterilized, especially by autoclaving at 120° C. or by beta or gamma irradiation of from 5 to 25 or 30 kGray, e.g. in a form frozen in the presence of dry ice. In order to facilitate its injection through fine needles, a lubricating agent, such as hyaluronic acid or gelatin, may be necessary, while still permitting the final sterilization. By way of variation, the fluidizing agent may be packaged in another, separate, syringe and may be sterilized independently by known means, such as autoclaving at 120° C. Mixing with the globin may then be effected using a sterile kit containing the two syringes of globin and fluidizing agent. These two syringes are equipped with a female luer end and may be connected by a sterile connector having two male luer ends. They are mixed homogeneously by pushing the contents of one syringe into the other and vice versa, effecting several reciprocating movements. Approximately ten reciprocating movements are generally sufficient to obtain a homogeneous viscous and pasty suspension ready to be injected.

Example 11

Preparation of a Soluble Dry Film from Chemically Modified Globin Soluble at pH 7.2

Application to the protection of wounds and the prevention of post-operative adhesion.

The foam or gel product prepared according to Example 9, omitting the addition of the crosslinking agent, may be deposited on a flat surface. After drying, a solid film is obtained whose thickness can be adjusted by the height of the deposit and whose pliability can be adjusted by adding a plasticizing agent, such as, for example, glycerol or polyethylene glycol. This film can be used in the protection or healing of internal or external wounds, either directly by spontaneous adhesion, or after fixing by an adhesive agent, such as oxidized starch, or by the application of a laser beam, if a colouring agent has been introduced into the film. In a variant, the initial gel may be cast, while incorporating a mesh constituted by resorbable or non-resorbable threads. In that case, the final membrane, obtained after drying, may be sutured. The film and the membrane have properties of preventing surgical adhesion.

Example 12

Preparation of an Insoluble Film from Globin that is Chemically Modified, Soluble at pH 7.2, and then Crosslinked by a Polyaldehyde Application to the protection of wounds and the prevention of post-operative adhesion.

The foam or gel product prepared in accordance with Example 9 may be deposited on a flat surface, to a specific thickness, before it sets. When crosslinking is complete, a solid film is obtained whose thickness can be adjusted by partial or total dehydration. This film can be used as in Example 11 in the protection or healing of internal or external wounds. It possesses properties of preventing surgical adhesion.

Example 13

Preparation of Solids by Moulding from the Crosslinked Adhesive Gels Obtained in Accordance with Example 9

Use as implants for the delayed release of medicaments in the organism.

The adhesive foam or gel prepared in accordance with Example 9 can be moulded in order to acquire the shape and volume desired for the implant. A medicament may be added to the mass in order to permit gradual and delayed release and to obtain a prolonged pharmacological effect.

Example 14

Medical Applications of the Implants of Chemically Modified Globin which are Secondarily Crosslinked in Order to Become Insoluble The chemically modified globin implants which are soluble or rendered insoluble by crosslinking, for example those prepared in accordance with any one of Examples 9, 10, 12 and 13, may be used in the following non-limiting applications:

Healing, protection or filling of external skin wounds or internal surgical wounds.

Filling of wrinkles and skin flaws.

Filling of connective tissue or sphincters for applications in urology: vesico-ureteral reflux in children, stress incontinence in women; in ENT: correction of vocal cord volume.

Adhesive and haemostatic plug for tissue wounds or percutaneous arterial wounds.

Means for fixing prostheses or biomaterials to receiver tissue, in particular for fixing devices for parietal and visceral reinforcement.

Films, gels and membranes for preventing post-operative adhesion, used alone or in combination with other medical devices.

Example 15

Medical Applications of the Chemically Modified Globin Implants Soluble at Physiological pH The soluble chemically modified globin implants, for example those prepared in accordance with any one of Examples 1 to 7, 9 and 11, may be used in the following non-limiting applications:

Skin healing, by using neutral and soluble powder by atomization or topical application onto the open wound. This application may be carried out directly from the powder or after dissolving in a physiological liquid or a fibrin glue.

This application may be in combination with other healing products or growth factors. A preferred formulation is a mixture of globin powder insoluble at physiological pH, prepared in accordance with the teaching of patent FR 2854801, and chemically modified globin powder soluble at physiological pH produced in accordance with the above Example 5.

The preferred proportion calculated in dry weight is from 30 to 10% of insoluble powder for from 70 to 90% of soluble powder. This powder becomes gradually impregnated with the natural exudate of the wound, by osmotic pumping owing to the soluble powder fraction which also stimulates colonization by fibrocytes. The insoluble powder fraction remains in the wound and inhibits the contraction thereof. The insoluble powder also helps to stimulate granulation tissue and the neosynthesis of collagen. It becomes incorporated in the granulation tissue before disappearing in one to two weeks by biodegradation.

Cartilage or bone healing by using chemically modified globin powder soluble at physiological pH, alone or in combination with other bone healing products: calcium phosphate, calcium carbonate, hydroxy apatite, growth factors of the BMP type, which may or may not be associated with insoluble globin powder prepared in accordance with the teaching of patent FR 2854801.

Association with antibiotics in order to inhibit the development of bacteria during the period of colonization and degradation of the implant.

The present invention therefore also relates to the use of a material which can be obtained from globin modified to be soluble at physiological pH, for the production of a preparation according to the invention suitable for the corresponding application.

In general, irrespective of the preparation according to the invention, the methods have a therapeutic aim. Methods for filling wrinkles may, depending on the persons concerned, have a purely cosmetic aim. In any case, the method according to the invention comprises the step of implanting locally, in or on the tissue of the patient or the person having need thereof, a therapeutically or cosmetically effective amount of a preparation according to the invention, in particular for the above-mentioned applications.

As described above, especially in Example 10, the preparations according to the invention, irrespective of their form, may preferably be sterilized by beta or gamma irradiation, preferably at from 5 to 25 or 30 kGray, e.g. in a form which is frozen, in particular in the presence of dry ice, preferably in their final packaging. The same applies to the globin preparations insoluble at neutral pH which are described in the applications or patents FR 2 854 801 and U.S. Pat. No. 6,949,652, which are incorporated herein by reference. When the preparations according to the invention or the applications and patents incorporated by reference comprise a mixture of globin and one or more components which can be sterilized at high temperature or by autoclaving, it is preferable to irradiate the globin and sterilize that or those components separately before mixing them in a sterile manner, for example, by using the syringes as described in Example 10. Thus, for example, it is possible to produce a sterile preparation in the form of a kit containing a syringe of a globin paste insoluble at physiological pH sterilized by irradiation, and a syringe of lubricating agent, for example, hyaluronic acid or hyaluronate sterilized by autoclaving, with the usual means for the sterile mixing of the contents of the two syringes.

BIBLIOGRAPHY

ANSON M. L.—MIRSKY A. E. (1930)
Protein Coagulation and its reversal. The preparation of insoluble globin, soluble globin and heme.
J. Gen. Physiol. 13, 469-476
AUTIO K—KIESVAARA M.—MALKKI Y.—KANKU S. (1984)
Chemical and functional properties of blood globin prepared by a new method
Journal of Food Science 49, 859-862
BERG J. W.—ORTMEYER D. W.—OTT D. L.—JACKSON R. L. (1953)
Comparison of Globin Insulin and NPH Insulin
Diabetes, 2, 5, p. 365-369
RABINOWITCH I. M.—FOWLER A. F.—BENSLEY E. H.—GORDON A. L.—MOUNTFORD M. (1947)
Globin Insulin
The Canadian Medical Association J., 56, 6, p. 595-605
REINER L. (1939)
Insulin preparation
U.S. Pat. No. 2,161,198
REINER L.—SEARLE D. S.—LANG E. H. (1939)
Insulin preparations with prolonged activity
I. Globin Insulin
Proc. Soc. Exp. Biol. Med. 40, p. 71
ROSSI-FANELLI A.—ANTONINI E.—CAPUTO A. (1958)
Studies on the structure of haemoglobin
I-Physicochemical properties of human globin
Biochem. Biophys. Acta 30, 608-615
SCHULZ F. N. (1898)
Der Eiweisskörper des hämoglobins [The albuminous body of haemoglobin]
Ztsch. F. physiol. chem. 24, 449-460
STRUMIA M. M.—SAMPLE A. B.—MAWR B. (1951)
Modified globin
I—Method for preparation from human erythrocytes.
J. Lab. and Clin. Med. 37, 959-968
STRUMIA M. M.—Mc GRAW J. J.—SAMPLE A. B.—MAWR B. (1952)
Modified globin
IV—Some of the physiological properties of modified human globin
J. Lab. and Clin. Med. 40, 2, 211-222
TAYOT J. L.—VERON J. L. (1983)
Brevet Institut Mérieux: FR 8311324
Process for preparing globin from haemoglobin and globin obtained by this process.
U.S. Pat. Nos. 4,543,209 (1985)
TEALE F. W. J. (1959)
Cleavage of the haem-protein link by acid methyl-ethyl keton
Biochem. Biophys. Acta 35, 543
VARS H. M.—BOXER G. E.—MAWR B. (1952)
Modified Globin
II—Chemical changes in human globin by alkaline modification
J. Lab. and Clin. Med. 39, 5, 743-751
VOLCKMANN H. (1988)

Essais de développement d'un substitut plasmatique d'origine placentaire. [Tests for the development of a plasma substitute of placental origin] Thèse d'ingénieur [Engineer's thesis] CNAM Lyon.

The invention claimed is:

1. An implantable preparation, comprising:
a material obtained from globin that has been chemically modified by alkaline treatment, and/or by acetylation or succinylation, or by esterification of its carboxylic groups, to be initially soluble at physiological pH, and further chemically modified to subsequently be substantially insoluble at said pH, said material being biocompatible and biodegradable in an organism and said preparation being in solid form selected from the group consisting of powder, granules, film, membrane, mesh, sponge and preformed implant, or in paste, gel, or suspension form.

2. The preparation according to claim 1, wherein the globin is a globin of human origin.

3. The preparation according to claim 1, wherein the insoluble material has been obtained by crosslinking the globin previously soluble at physiological pH.

4. The preparation according to claim 3, wherein the crosslinking is carried out by 1,4-butanediol diglycidyl ether, for acetyl or succinyl globin.

5. The preparation according to claim 1, being in solid form, selected from the group consisting of powder, granules, film, membrane, mesh, sponge and preformed implant form, further comprising additional globin that has been chemically modified to be soluble at physiological pH, said additional globin being biocompatible and biodegradable in said organism.

6. The preparation according to claim 1, further comprising a filling material, which is biocompatible and sterile and insoluble at physiological pH.

7. The preparation according to claim 6, wherein said filling material comprises sterile biodegradable globin insoluble at physiological pH.

8. The preparation according to claim 6, wherein said filling material is selected from the group consisting of collagens, chitosan and oxidized celluloses.

9. The preparation according to claim 1, which is in the form of an injectable suspension, paste or gel.

10. The preparation according to claim 1, which is in solid powder form.

11. The preparation according to claim 1, which is in one of the forms selected from the group consisting of:
powder,
granules,
film, membrane, mesh,
sponge, and
preformed implant.

12. An implantable preparation, comprising:
a material comprising globin that has been chemically modified by alkaline treatment, and/or by acetylation or succinylation, or by esterification of its carboxylic groups, to be, at least partially, soluble at physiological pH, said material being biocompatible and biodegradable in an organism and in powder form, and
a material selected from the group consisting of:
a crosslinking agent, to form, with said globin chemically modified to be soluble, at least partially, at physiological pH, a glue which adheres to organic tissue,
a solid material insoluble at physiological pH obtained from globin, and
a solid dressing.

13. The preparation according to claim 12, wherein the crosslinking agent is itself in the form of a powder, it being possible for said globin that has been chemically modified to be at least partially soluble, and said crosslinking agent to form a glue in the presence of a liquid medium.

14. The preparation according to claim 12, wherein said solid material comprises sterile biodegradable globin insoluble at physiological pH.

15. The preparation according to claim 12, wherein said solid material is in the form of a powder.

16. The preparation according to claim 13, formulated in the form of a dry spray.

17. The preparation according to claim 11, which comprises globin chemically modified to be at least partially soluble at physiological pH.

18. The preparation according to claim 17, which is produced in the form of a woven fabric, a knitted fabric, a mesh, a sponge or a film, which are implantable and optionally reinforced by a suturable implantable material.

19. The preparation according to claim 17, which comprises another biocompatible solid material.

20. The preparation according to claim 17, which further comprises sterile biodegradable globin insoluble at physiological pH.

21. The preparation according to claim 10, which is produced in the form of a dry spray.

22. The preparation according to claim 1, which is produced in the form of a solid implant obtained by crosslinking a gel or a foam of globin chemically modified to be soluble at physiological pH.

23. The preparation according to claim 1, which comprises a fluidizing agent and is in the form of a suspension, paste or gel.

24. The preparation according to claim 23, wherein the fluidizing agent comprises hyaluronic, carboxymethylcellulose or gelatin.

25. The preparation according to claim 23, wherein the fluidizing agent comprises globin modified to be at least partially soluble at physiological pH.

26. An implantable glue preparation, comprising:
a material obtained from globin that has been chemically modified by alkaline treatment, and/or by acetylation or succinylation, or by esterification of its carboxylic groups, to be, at least partially, soluble at physiological pH, said material being biocompatible and biodegradable in an organism, said preparation comprising an adhesive agent being hyaluronic acid or carboxymethylcellulose.

27. The preparation according to claim 12, for forming a biological glue, which is in the form of a kit comprising, in separate containers, said globin powder soluble at physiological pH and said crosslinking agent.

28. The preparation according to claim 1, which is sterile.

29. The preparation according to claim 28, wherein at least the material obtained from globin chemically modified to be at least partially soluble at physiological pH has been sterilized by beta or gamma irradiation, at from 5 to 30 kGray, optionally in a form which is frozen, optionally in the presence of dry ice.

30. The preparation according to claim 29, which comprises at least one other material which has been sterilized at high temperature.

31. The preparation according to claim 1, wherein the globin has been chemically modified by methylation or ethylation.

32. The preparation according to claim 3, wherein this crosslinking is carried out by glutaraldehyde, or a polysaccharide oxidized in the form of macromolecular polyaldehyde, when said material obtained from globin and soluble at physiological pH is an ester of globin or a derivative obtained by alkaline treatment.

33. The preparation according to claim 19, wherein said another biocompatible solid material is selected from the group consisting of collagen, chitosan and oxidized cellulose.

34. A method for the filling of wrinkles or skin flaws comprising the step of injecting locally in a tissue of a patient in need thereof, an effective amount of an implantable preparation, comprising a material which can be obtained from globin that has been chemically modified by alkaline treatment, and/or by acetylation or succinylation, or by esterification of its carboxylic groups, to be, at least partially, soluble at physiological pH, said material being biocompatible and biodegradable in an organism, said preparation being in solid, paste, gel, suspension or solution form, provided that, when the preparation is in the form of an injectable solution and said globin that has been modified forms a main active constituent, the concentration of said modified globin is at least 10%.

35. A method for healing, protecting or filling external skin wounds or internal surgical wounds comprising the step of implanting locally in a tissue of a patient in need thereof, an effective amount of an implantable preparation, comprising a material which can be obtained from globin that has been chemically modified by alkaline treatment, and/or by acetylation or succinylation, or by esterification of its carboxylic groups, to be, at least partially, soluble at physiological pH, said material being biocompatible and biodegradable in an organism, said preparation being in solid, paste, gel, suspension or solution form, provided that, when the preparation is in the form of an injectable solution and said globin that has been modified forms a main active constituent, the concentration of said modified globin is at least of 10%.

36. A method for filling of connective tissue or sphincters for applications in urology, in ear, nose and throat surgery, or for the formation of an adhesive and homeostatic plug for tissue wounds or percutaneous arterial wounds, or for fixing prostheses or biomaterials to receiver tissue, or for preventing post-operative adhesion by implantation of films, gels and membranes, used alone or in combination with other medical devices, or for the healing of cartilage or bone, comprising the step of implanting locally in or on a tissue of a patient in need thereof, an effective amount of an implantable preparation, comprising a material which can be obtained from globin that has been chemically modified by alkaline treatment, and/or by acetylation or succinylation, or by esterification of its carboxylic groups, to be, at least partially, soluble at physiological pH, said material being biocompatible and biodegradable in an organism, said preparation being in solid, paste, gel, suspension or solution form, provided that, when the preparation is in the form of an injectable solution and said globin that has been modified forms a main active constituent, the concentration of said modified globin is at least 10%.

37. The method according to claim 36, wherein the method is adapted for fixing devices for parietal or visceral reinforcement.

38. An implantable glue preparation, comprising:
a material obtained from globin that has been chemically modified by alkaline treatment, and/or by acetylation or succinylation, or by esterification of its carboxylic groups, to be, at least partially, soluble at physiological pH, said material being biocompatible and biodegradable in an organism; and
a crosslinking agent, wherein said implantable glue preparation is in the form of a foam.

\* \* \* \* \*